United States Patent
Kapries et al.

[11] Patent Number: 5,817,851
[45] Date of Patent: Oct. 6, 1998

[54] MONOVINYLTIN TRIHALIDES AND PROCESS FOR THEIR PREPARATION

[75] Inventors: Andrea Kapries, Ascheberg-Herbern; Ulrich Stewen, Schwerte; Udo Weinberg, Bergkamen, all of Germany

[73] Assignee: Witco GmbH, Bergkamen, Germany

[21] Appl. No.: 874,764

[22] Filed: Jun. 13, 1997

[30] Foreign Application Priority Data

Jun. 25, 1996 [EP] European Pat. Off. ............ 962017703

[51] Int. Cl.$^6$ ...................................... C07F 7/22
[52] U.S. Cl. ................................. 556/87; 556/81
[58] Field of Search ......................................... 556/87, 81

[56] References Cited

U.S. PATENT DOCUMENTS 4,324,737  4/1982  Foure .

FOREIGN PATENT DOCUMENTS 27 48 370 A 1  5/1979  Germany .

OTHER PUBLICATIONS

Konrad Von Werner, Hermann Blank, Journal of Organometallic Chemistry, 165 (1979) 187–198.

*Primary Examiner*—Gary Geist
*Assistant Examiner*—Jean Vollano
*Attorney, Agent, or Firm*—Scully, Scott, Murphy & Presser

[57] ABSTRACT

Disclosed are monovinyltin trihalides of he general formula (I):

$$(x)(x^1)(x^2)Sn\text{—}C(R)\text{=}C(R^1)\text{—}C(O)\text{—}R^2 \qquad (I)$$

and a process for their preparation from 1,3-diketones, tin(II) halides and halogen acids.

8 Claims, No Drawings

MONOVINYLTIN TRIHALIDES AND PROCESS FOR THEIR PREPARATION

FIELD OF THE INVENTION

The invention relates to novel monovinyltin trihalides from 1,3-diketones, tin (II) halides and halogen acids and to a process for the preparation of the novel monovinyltin trihalides.

BACKGROUND OF THE INVENTION

Organic tin compounds have been established for many years as a regular constituent of formulations in the pesticide and antifouling agent sectors, as stabilizers for thermoplastics, especially vinyl chloride polymers or copolymers, as catalysts for the manufacture of polyurethanes or silicone resins, and for the production of doped or undoped $SnO_2$ coatings on glass or ceramic surfaces.

The overwhelming number of published processes produce compounds which do not contain vinyl groups bonded to tin and which are thus excluded from further possible reactions of interest.

Processes for the preparation of organotin compounds with vinyl groups directly bonded to tin are known for example from W. P. Neumann, Die organische Chemie des Zinns (The Organic Chemistry of Tin), Ferdinand Enke Verlag, Stuttgart, 1967; P. G. Harrison, Chemistry of Tin, Blackie, Glasgow and London, 1989; M. Pereyre, J. P. Quintard and A. Rahm, Tin in Organic Synthesis, Butterworth, London, 1987; R. C. Poller, The Chemistry of Organotin Compounds, Logos Press Limited, 1970; W. P. Neumann, Synthesis, 1987, 665; T. N. Mitchell, Synthesis, 1992, 803; and I. Omae, Organotin Chemistry, Elsevier, Amsterdam, 1989.

The following synthesis variants are described in said publications:

- alkylation of $SnCl_4$ or organotin compounds with vinyl-Grignard or vinyllithium compounds;
- hydrostannation of substituted acetylene derivatives;
- additions of triorganotin-metal compounds (e.g. $R_3SnSnR_3$, $R_3SnSiR_3$, $Bu_3SnAlEt_2$, $(Bu_3Sn)_2Zn$);
- α, β-elimination of appropriately substituted alkyl radicals bonded to tin.

A common feature of all these variants is that they are very expensive and are therefore unsuitable or of only limited suitability for industrial scale production.

DE-OS 27 48 370 and J. Organomet. Chem., 165 (1979) 187–198, have disclosed a process for the preparation of vinyltin trihalides wherein acetylenecarboxylic acid esters are reacted with tin (II) halides and hydrogen halides in the presence of polar organic solvents, for reaction times of 10–40 hours, to give vinyltin compounds containing carboxylic acid ester groups.

BRIEF SUMMARY OF THE INVENTION

It has now been found that vinyltin compounds of the general formula (I):

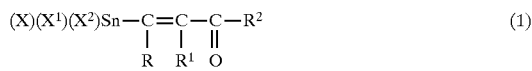

(1)

in which R and $R^2$, which are identical or different, can be optionally substituted alkyl groups having 1–5 C atoms, cycloalkyl groups having 5–10 C atoms, aryl groups having 6–12 C atoms and alkylaryl groups and/or arylalkyl groups having 7–12 C atoms, $R^1$ is H, R or $R^2$ and X, $X^1$ and $X^2$, which are identical or different, can be chlorine, bromine and iodine, are obtained in adequate purity under practical conditions, in short reaction times and without expensive working-up times, by reacting compounds of the general formula II:

(II)

in which R, $R^1$ and $R^2$ are as defined above, R and $R^2$ preferably being a methyl radical or phenyl radical and $R^1$ preferably being hydrogen, with anhydrous tin(II) chloride, bromide or iodide, optionally in the presence of an inert solvent such as ethers or aliphatic hydrocarbons, at -10° to 100° C., preferably 20°–50° C., and with halogen acids of the general formula III:

(III)

in which X can be Cl, Br or I and $R^3$ can be H or the radical —$COR^4$, where $R^4$ can be —$R^5$—$CH_3$, —$R^5$—CO—X, in which $R^5$=—$(CH_2)_n$—, where n=0–10, preferably 0–5, or $R^3$ can be an optionally substituted cycloaliphatic, araliphatic or aromatic radical.

DETAILED DESCRIPTION OF THE INVENTION

The reaction times are between 0.5 and 5 h at the preferred reaction temperature of 20°–50° C., but are normally below 3 h in the range 1.5–2.5 h.

Suitable solvents which can optionally be used are aliphatic, cycloaliphatic or cyclic ether such as, in particular, diethyl ether, tetrahydrofuran or dioxane, and optionally halogenated hydrocarbons such as pentane, hexane, heptane, octane, decane or their isomers, methylene chloride, chloroform, carbon tetrachloride, dichloroethylene or perchloroethylene. It is preferable to use the relatively low boiling, toxicologically harmless, pure hydrocarbons having 6–10 C atoms and dialkyl ethers having 4–8 C atoms.

The tin(II) halides used according to the invention are commercially available products with purities of >95%.

The inorganic and/or organic halogen acids used according to the invention include hydrogen chloride, hydrogen bromide, hydrogen iodide and the acid halides of the organic homologous series of monocarboxylic and polycarboxylic acids, such as, in particular, acetyl chloride, propionyl chloride, butyryl chloride, valeroyl chloride, octyl chloride, malonyl chloride or succinyl chloride.

Cycloaliphatic and aromatic acid halides, derived from benzoic acid, phthalic acid, isophthalic acid, terephthalic acid, phenylenediaceticacid and their hexahydro variants, can also be used.

The acid chlorides of the short chain monocarboxylic acids, such as, in particular, acetyl chloride, n-propionyl chloride, n-butyryl chloride or benzoyl chloride, are preferred according to the invention.

The reaction can be carried out within a wide temperature range from -10° to 100° C., optionally at normal pressure at the reflux point of the solvent or optionally in a pressure reactor at the autogeneous system pressure.

To avoid secondary reactions and for reasons of process technology, such as reaction times and process control in particular, preferred reaction temperatures are 10°–80°, especially 20°–50° C., at normal pressure.

In the procedure preferred according to the invention, a tin(II) halide, preferably tin(II) chloride, a 1,3-diketone of the general formula II and optionally a solvent are placed in a reactor at room temperature, under an inert gas and with the exclusion of moisture, and the halogen acid or the acid halides preferred according to the invention are metered into the vigorously mixed reaction mixture.

During this process the reaction temperature can be controlled by the metering rate and/or by auxiliary external cooling or by evaporative cooling at the reflux point of the solvent.

After the halogen acid has been added, a postreaction time of 2–3 hours at the given reaction temperature, with continuous thorough mixing (e.g. stirring), is normally sufficient to complete the reaction.

The tin(II) halide, the compound of the formula II and the halogen acid of the formula III are preferably used in equimolar proportions according to the equation

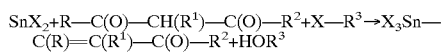
$$SnX_2 + R—C(O)—CH(R^1)—C(O)—R^2 + X—R^3 \rightarrow X_3Sn—$$
$$C(R)=C(R^1)—C(O)—R^2 + HOR^3$$

in which the substituents are defined as indicated. Although it is possible to use the individual components in excess, this is not preferred according to the invention because it could necessitate additional purification steps for the end product.

If solvents are used, their amount is proportioned so as to ensure perfect process control (thorough mixing, dissipation of the heat of reaction). However, because the reaction product should precipitate from the reaction mixture as quantitatively as possible, the amount of solvent has to be adapted to the solubility product.

When working under reflux conditions, all or part of the solvent can therefore already be distilled off, optionally below normal pressure and optionally with the aid of a carrier gas passed through the reaction mixture, it also being possible to remove the compound $HOR^3$ formed according to the equation, provided said compound distills under the given conditions.

If the reaction product is obtained immediately as a solid precipitate, it can be separated from by-products like $HOR^3$ by conventional methods (e.g. filtration) and solvents which are still present can be removed by drying. As a rule the purity of the resulting product is adequate for further use. Very high purities are achieved by rinsing again one or more times with a small amount of solvent.

If the end product is obtained as a viscous or partially crystalline mixture—when the reaction is carried out without a solvent or after the solvent has already been removed from the reaction mixture at an earlier stage—crystallization can be accelerated by the addition of small amounts of ethers or hydrocarbons, by-products like $HOR^3$ then being removable at the same time.

An aftertreatment with absorbents like activated charcoal is generally no longer necessary.

The compounds of the general formula I according to the invention are valuable intermediates for the manufacture of novel pesticides and antifouling paints, in which they can be incorporated into the possibly polymeric structure, as comonomers with a catalytic action or as catalysts in the manufacture of polyurethane foams or silicone compositions.

The process for the preparation of the compounds of the general formula (I) according to the invention will be illustrated in greater detail by means of the following examples.

EXAMPLES

Example 1

94.8 g (0.5 mol) of tin(II) chloride and 50 g (0.5 mol) of acetylacetone in 200 ml of diethyl ether were placed in a reactor at room temperature. 39.3 g (0.5 mol) of acetyl chloride were metered in over 15 min, the temperature rising to 36° C. After a postreaction time of 2 h at room temperature, the white crystals which had precipitated out were filtered off and washed twice with 50 ml of diethyl ether. After drying under vacuum, 88 g (57% of theory) of 1-methylbut-1-en-3-onyltin trichloride ($Cl_3Sn—C(CH_3)=CH—CO—CH_3$) melting at 129°–130° C. were isolated.

A further 45 g (29% of theory) could be precipitated from the mother liquor by the addition of 200 ml of n-pentane.

$^1H$ NMR ($CDCl_3$): $\delta=2.51$ (s, 3H, $Sn—C(CH_3)=C$, $^3J_{Sn}=144$ Hz), 2.63 (s,3H, CO—$CH_3$), 7.24–7.29 (m, 1H, $H_{vinyl}$, $^3J_{Sn}=420$ Hz)

$^{13}C$ NMR ($CDCl_3$): $\delta=22.3$ (=C—$CH_3$), 28.6 (CO—$H_3$), 133.9 (C=CH), 168.4 (=C—$CH_3$), 201.1 (C=O)

Example 2

94.8 g (0.5 mol) of tin(II) chloride and 50 g (0.5 mol) of acetylacetone in 200 ml of n-pentane were placed in a reactor at room temperature. 61 g (0.5 mol) of acetyl bromide were metered in over 15 min. After a postreaction time of 2 h at room temperature the crystals which had precipitated out were separated off, washed with diethyl ether and dried under vacuum.

141 g (80% of theory) of 1-methylbut-1-en-3-onyltin bromide dichloride ($BrCl_2Sn—C(CH_3)=CH—CO—CH_3$) melting at 119° C. were isolated. The yield was increased to >95% by concentration of the mother liquor and repeat crystallization.

Example 3

94.8 g (0.5 mol) of tin(II) chloride and 50 g (0.5 mol) of acetylacetone were placed in a reactor at room temperature. 39.3 g (0.5 mol) of acetyl chloride were metered in over 45 min, the temperature rising to 45° C. The highly viscous, partially crystalline reaction mixture was stirred for 2 h, 50 ml of n-pentane were added and the solid formed was separated off. After washing with 100 ml of n-pentane and drying, 140 g (92% of theory) of 1-methylbut-1-en-3-onyltin trichloride were isolated.

Example 4

94.8 g (0.5 mol) of tin(II) chloride and 81.1 g (0.5 mol) of benzoylacetone in 200 ml of diethyl ether were placed in a reactor at room temperature. 39.3 g (0.5 mol) of acetyl chloride were metered in over 15 min, a rise in temperature to 36° C. being recorded. After a postreaction time of 2 h at room temperature, the light yellow crystalline precipitate which had formed was separated off, washed twice with 50 ml of diethyl ether and dried under vacuum.

110 g (60% of theory) of 1-methylprop-1-en-3-onyl-3-phenyltin trichloride ($Cl_3Sn—C(CH_3)=CH—CO—Ph$) melting at 206°–208° C. were isolated, the yield being increased to >90% by concentration of the mother liquor. Cl content: found 28.3%; theoretical 28.7%

$^1H$ NMR (acetone—$d_6$): $\delta=2.55$ (s,3H, $Sn—C(CH_3)=C$, $^3J_{Sn}=148$ Hz), 7.68–8.47 (m,5$H_{arom}$, 1$H_{vinyl}$)

$^{13}C$ NMR (acetone—$d_6$): $\delta=22.2$ (=C—$CH_3$), 125.3, 130.7 131.8, 133.7 ($C_{arom}$), 137.9 (C=C—H), 185.1 (=C—$CH_3$), 191.7 (C=O)

Example 5

94.8 g (0.5 mol) of tin(II) chloride in 200 ml of diethyl ether were placed in a reactor and 81.1 g (0.5 mol) of benzoylacetone were added. 61 g (0.5 mol) of acetyl bromide were metered in over 15 min, the reaction temperature rising to 38° C. After a postreaction time of 2 h at room temperature, the light yellow crystalline precipitate was filtered off, washed with a small amount (2×20 ml) of diethyl ether and dried under vacuum.

104 g (50% of theory) of 1-methylprop-1-en-3-onyl-3-phenyltin bromide dichloride ($BrCl_2Sn$—$C(CH_3)$=$CH$—$CO$—$Ph$) melting at 199°–201° C. were isolated, the yield being increased to >90% by working-up of the mother liquor. Sn content: found 28.3%; theoretical 28.6%.

Example 6

94.8 g (0.5 mol) of tin(II) chloride in 200 ml of diethyl ether were placed in a reactor and 50 g (0.5 mol) of acetylacetone were added. 70 g (0.5 mol) of benzoyl chloride were metered in over 15 min, the temperature rising to 30° C. After a postreaction time of 3 h at the reflux temperature, the white crystalline precipitate was separated off and dried under vacuum.

113 g (73% of theory) of 1-methylbut-1-en-3-onyltin trichloride melting at 128°–129° C. were isolated.

Example 7

The procedure was analogous to Example 6 except that the benzoyl chloride was replaced with 45.3 g (0.5 mol) of acryloyl chloride. The yield was 80% of theory.

Example 8

The procedure was analogous to Example 6 except that the benzoyl chloride was replaced with 38.7 g (0.26 mol) of cyclohexanecarboxylic acid chloride. The yield of directly precipitated product was 41 g (50% of theory), which was increased to >95% of theory by further concentration of the filtrate.

Example 9

The procedure was analogous to Example 6 except that the 0.5 mol of benzoyl chloride was replaced with 0.25 mol of phthaloyl dichloride. The yield was ca. 90% by the product was contaminated with phthalic acid.

Example 10

The procedure was analogous to Example 6. 50 g (0.26 mol) of tin(II) chloride and 25.6 g (0.26 mol) of acetylacetone was reacted with 44 g (0.26 mol) of cinnamoyl chloride in 150 ml of diethyl ether to give a quantitative yield of 81.4 g of 1-methylbut-1-en-3-onyltin trichloride.

Example 11

39.8 g (0.21 mol) of tin(II) chloride and 21.0 g (0.21 mol) of acetylacetone in 200 ml of diethyl ether were placed in a reactor. 38.8 g (0.21 mol) of benzoyl bromide were metered in over 15 min at room temperature, with stirring, a rise in temperature to the reflux point being recorded. After a postreaction time of 1 h at the reflux temperature, the mixture was cooled and the crystalline precipitate was separated off. 48 g (65% of theory) of 1-methylbut-1-en-3-onyltin bromide dichloride ($BrCl_2Sn$—$C(CH_3)$=$CH$—$CO$—$CH_3$) were isolated.

$^1$H NMR ($CDCl_3$: $\delta$=2.51 (s, 3H, Sn—$C(CH_3)$=C, $^3J_{Sn}$=140 Hz, 2.63 (s, 3H, CO—$CH_3$), 7.16–7.25 (m, 1H, $H_{vinyl}$)

$^{13}$C NMR ($CDCl_3$): $\delta$=22.3 (=C—$CH_3$, $^2J_{Sn}$=97 Hz), 28.7 (CO—$CH_3$), 133.7 (C=CH, $^2J_{Sn}$=89 Hz), 168.8 (=C—$CH_3$, $^1J_{Sn}$=1006 Hz), 200.8 (C=0, $^3J_{Sn}$=83 Hz)

Example 12

The procedure was analogous to Example 6. 22.4 g (0.08 mol) of tin(II) bromide and 8.0 g (0.08 mol) of acetylacetone were reacted with 9.8 g (0.08 mol) of acetyl bromide in 200 ml of diethyl ether and the reaction solution was concentrated to give 34.0 g (96% of theory) of 1-methylbut-1-en-3-onyltin tribromide ($Br_3Sn$—$C(CH_3)$=$CH$—$CO$—$CH_3$) melting at 110°–112° C.

$^1$H NMR ($CDCl_3$): $\delta$=2.47 (s, 3H, Sn—$C(CH_3)$=C, $^3J_{Sn}$=140 hz), 2.63 (s, 3H, CO—$CH_3$), 7.09–7.11 (m, 1H, $H_{vinyl}$, $^3J_{Sn}$=391; 407 hz)

$^{13}$C NMR ($CDCl_3$): $\delta$=22.3 (=C—$CH_3$, $^2J_{Sn}$=96 hz), 28.9 (CO—$CH_3$), 133.7 (C=CH, $^2J_{Sn}$=77 Hz), 168.2 (=C—$CH_3$), 200.7 (C=O)

Example 13

The procedure was analogous to Example 6. 26.6 g (0.096 mol) of tin(II) bromide and 9.6 g (0.096 mol) of acetylacetone were reacted with 7.6 g (0.096 mol) of acetyl chloride in 200 ml of diethyl ether and the reaction solution was concentrated to give 36.4 g (96% of theory) of 1-methylbut-1-en-3-onyltin dibromide chloride ($Br_2ClSn$—$C(CH_3)$=$CH$—$CO$—$CH_3$) melting at 112°–115° C.

$^1$H NMR ($CDCl_3$): $\delta$=2.48 (s, 3H, Sn—$C(CH_3)$=C, $^3J_{Sn}$=140 hz), 2.63 (s, 3H, CO—$CH_3$), 7.08–7.22 (m, 1, $H_{vinyl}$)

$^{13}$C NMR ($CDCl_3$): $\delta$=22.4 (=C—$CH_3$, $^2J_{Sn}$=96 Hz), 28.9 (CO—$CH_3$), 133.3 (C=CH, $^2J_{Sn}$=78 Hz), 168.8 (=C—$CH_3$), 200.8 (C=O)

We claim:

1. A compound of the following formula (I):

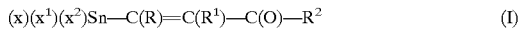

in which R and $R^2$ are identical or different and each is an optionally substituted hydrocarbon, $R^1$ is H or any group that R is, and X, $X^1$ and $X^2$ are identical or different and each is chlorine, bromine or iodine.

2. A compound according to claim 1 of the general formula (I) in which R and $R^2$ are identical or different and each is selected from the group consisting of optionally substituted alkyl groups having 1–5 C atoms, aryl groups having 6–12 C atoms, and alkylaryl and arylalkyl groups having 7–12 C atoms; and each of X, $X^1$ and $X^2$ is chlorine or bromine.

3. A compound according to claim 1 of the general formula (I) in which R and $R^2$ are methyl groups, $R^1$ is hydrogen and X, $X^1$ and $X^2$ are identical or different and each is chlorine or bromine.

4. A process for the preparation of a compound of the general formula

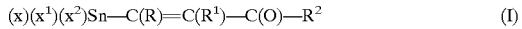

in which R and $R^2$ are identical or different and each is an optionally substituted hydrocarbon, $R^1$ is H or any group that R is, and X , $X^1$ and $X^2$ are identical or different and each is chlorine, bromine or iodine, comprising reacting a compound of the general formula II:

in which R, $R^1$ and $R^2$ are as defined above with a compound of the formula $SnX_2$ (IV), in which X is chlorine, bromine or iodine, optionally in the presence of an inert, anhydrous organic solvent, and with one or more halogen acids of the general formula X—$R^3$ (III), in which X is chlorine, bromine or iodine and $R^3$ is the radical —C(O)—$R^4$ where $R^4$ is —$R^5$—$CH_3$ or —$R^5$—C(O)X, in which $R^5$=—$(CH_2)_n$—, where n is 0–10, or $R^4$ is an optionally substituted cycloaliphatic, aromatic or araliphatic radical, at a temperature of 0°–100° C., and subsequently isolating the compound of the general formula (I).

5. The process as claimed in claim 4 wherein, in the compounds of the general formula (II), R and $R^2$ are identical or different and each is selected from the group consisting of optionally substituted alkyl groups having 1–5 C atoms, aryl groups having 6–12 C atoms, and alkylaryl and arylalkyl groups having 7–12 C atoms; and X, $X^1$ and $X^2$ is each chlorine, bromine or iodine.

6. The process as claimed in claim 5 wherein in the compounds of the general formula (II), R and $R^2$ are methyl groups, $R^1$ is hydrogen and X, $X^1$ and $X^2$ are identical or different and each is chlorine or bromine.

7. The process as claimed in claim 6 wherein said one or more halogen acids have the general formula X—$R^3$ (III) in which $R^3$ is an acyl group having 1–4 C atoms or a benzoyl radical, and X is chlorine, bromine or iodine.

8. The process as claimed in claim 7 wherein the reaction is carried out in the presence of an ether or a hydrocarbon or a chlorinated hydrocarbon at a temperature of 10°–80° C.

* * * * *

UNITED STATES PATENT AND TRADEMARK OFFICE
CERTIFICATE OF CORRECTION

PATENT NO. : 5,817,851
DATED : October 6, 1998
INVENTOR(S) : Andrea Kapries, et al.

It is certified that error appears in the above-identified patent and that said Letters Patent are hereby corrected as shown below:

Column 2, Line 32: "ether" should read --ethers--

Signed and Sealed this

Twenty-ninth Day of May, 2001

Attest:

NICHOLAS P. GODICI

*Attesting Officer*  *Acting Director of the United States Patent and Trademark Office*